United States Patent [19]

Walker et al.

[11] 4,357,279
[45] Nov. 2, 1982

[54] PREPARATION OF CORTICOIDS FROM 17-KETO STEROIDS

[75] Inventors: Jerry A. Walker; Edward J. Hessler, both of Kalamazoo, Mich.

[73] Assignee: The Upjohn Company, Kalamazoo, Mich.

[21] Appl. No.: 264,593

[22] Filed: May 18, 1981

[51] Int. Cl.³ .................................................. C07J 7/00
[52] U.S. Cl. ........................... 260/397.45; 260/239.5; 260/397.5
[58] Field of Search .................................... 260/397.45

[56] References Cited

U.S. PATENT DOCUMENTS

| | | | |
|---|---|---|---|
| 3,684,657 | 8/1972 | Kraychy et al. | 195/51 |
| 3,759,791 | 9/1973 | Marshack et al. | 195/51 |
| 4,035,236 | 7/1977 | Wovcha | 195/51 G |
| 4,041,055 | 8/1977 | Shephard et al. | 260/397.3 |
| 4,216,159 | 8/1980 | Hessler et al. | 260/397.1 |

OTHER PUBLICATIONS

J. Am. Chem. Soc. 86, 3840 (1964).
J. Org. Chem. 35, 2831 (1970).

Primary Examiner—Elbert L. Roberts
Attorney, Agent, or Firm—Bruce Stein

[57] ABSTRACT

A process for the preparation of corticoids (XI) which comprises reacting a protected 17-keto steroid (II) with a metallated 1,2-dihaloethene (III).

11 Claims, No Drawings

PREPARATION OF CORTICOIDS FROM 17-KETO STEROIDS

DESCRIPTION

BACKGROUND OF THE INVENTION

In the past few years, 17-keto steroids have become much more readily available as starting materials for corticoid synthesis because of the discovery of a number of microorganisms which will cleave the $C_{17}$ side chain of various steroid substrates, see U.S. Pat. Nos. 4,035,236, 3,684,657 and 3,759,791.

U.S. Pat. No. 4,041,055 claims a process for producing 17α-hydroxyprogesterone and corticoids from 17-keto steroids. The first step is addition of a 2-carbon moiety by formation of ethisterone. This is followed (1) by reaction with phenylsulfenyl chloride to form an allene sulfoxide, (2) Michael addition to form a sulfoxide, (3) reaction with a thiophile and (4) reaction with a peracid to give the 17α,21-dihydroxy-20-keto corticoid side-chain.

U.S. Pat. No. 4,216,159 claims a process of transforming a 17-keto steroid to the corresponding 16-unsaturated-21-hydroxy-20-keto steroid by reaction with a lithiated chlorovinyl ether. The objective of that patent is to produce $\Delta^{16}$-$C_{21}$ steroids which can then be used to make $C_{16}$ functionalized corticoids.

The process of the present invention does not involve lithiated chloro vinyl ethers and does not produce $\Delta^{16}$-$C_{21}$ steroids.

The process of the present invention is similar to the process of U.S. Pat. No. 4,041,055 in that it transforms a 17-keto steroid to the corresponding corticoid, but does so by a different synthetic pathway.

The base catalyzed isomerization of $\beta$, $\gamma$ to $\alpha,\beta$-unsaturated sulfoxides is well known, see J. Am. Chem. Soc. 86, 3840 (1964) and the addition of nucleophiles to $\beta$-halo-$\alpha,\beta$-unsaturated sulfoxides has been previously observed in simple systems, see J. Org. Chem. 35, 2831 (1970).

SUMMARY OF THE INVENTION

Refer to Charts A-E.

Disclosed is a process for the preparation of a corticoid of formula (XI) which comprises (1) contacting a protected 17-keto steroid selected from the group consisting of compounds of formulas (IIa–IIe) with a metallated 1,2-dihalogenated ethene (III) to form the corresponding protected $C_{21}$-steroid selected from the group consisting of compounds of formulas (IVa-IVe) respectively; (2) hydrolyzing the protected $C_{21}$-steroid (IVa-IVe) with acid to remove the protecting group and give a $C_{21}$-steroid (V); (3) contacting the $C_{21}$-steroid (V) with a sulfenylating agent (VI) to give a 20,21-dihalo steroid (VII); (4) contacting the 20,21-dihalo steroid (VII) with a base selected from the group consisting of an alkoxide or mercaptide ($OR_{20}^-$ or $SR_{20}^-$) respectively, to give a sulfoxide (VIII); (5) contacting the sulfoxide (VIII) with a thiophile to give a 20-unsaturated steroid (IX); (6) hydrolyzing the 20-unsaturated steroid (IX) with acid to give a 21-halo steroid (X) and (7) contacting the 21-halo steroid (X) with an anion ($R_{21}CO_2^{\ominus}$).

Also disclosed is a process for the preparation of the 21-halo steroid (X) which comprises starting with the protected 17-keto steroid (IIa–IIe) and following steps (1)–(6) above.

Further disclosed is a process for the preparation of the 20-unsaturated steroid (IX) which comprises starting with the protected 17-keto steroid (IIa–IIe) and following steps (1)–(5) above.

Disclosed is a process for the preparation of the $C_{21}$-steroid (V) which comprises starting with the protected 17-keto sterid (IIa–IIe) and following steps (1) and (2) above.

Also disclosed is a process for the preparation of the 20,21-dihalo steroid (VII) which comprises contacting the $C_{21}$-steroid (V) with a sulfenylating agent (VI).

Further disclosed is a process for the preparation of the sulfoxide (VIII) which comprises contacting the 20,21-dihalo steroid (VII) with an alkoxide or mercaptide ($OR_{20}^{\ominus}$ or $SR_{20}^{\ominus}$).

Disclosed is a process for the preparation of the 20-unsaturated steroid (IX) which comprises starting with the 20,21-dihalo steroid (VII) and following steps (4) and (5) above.

Also disclosed is a process for the preparation of the 21-halo steroid (X) which comprises starting with the 20,21-dihalo steroid (VII) and following steps (4)–(6) above.

Disclosed are the novel intermediates, the protected $C_{21}$-steroid (IVa–IVe), the $C_{21}$-steroid (V), the 20,21-dihalo steroid (VII), the sulfoxide (VIII) and the 20-unsaturated steroid (IX).

DETAILED DESCRIPTION OF THE INVENTION

Charts A–C disclose the process of the present invention.

For the 17-keto steroid (I) starting material, $R_6$ is a hydrogen or fluorine atom or methyl group. It is preferred that $R_6$ is a hydrogen atom. $R_9$ is a hydrogen or fluorine atom, hydroxyl or $-OSi(R)_3$ group or nothing. It is preferred that $R_9$ is nothing, giving a $\Delta^{9(11)}$ double bond. $R_{11}$ is [H], [H,H], [H, $\beta$-OH] or [H, $\beta$-OSi(R)$_3$]. It is preferred that $R_{11}$ is [H]. $R_{16}$ is a hydrogen atom or methyl group. It is preferred that $R_{16}$ is a hydrogen atom.

The 17-keto steroid (I) starting materials are well known to those skilled in the art or may readily be prepared from known compounds by methods well known to those skilled in the art. For example, the $\Delta^{1,4}$-17-keto steroids (I) are known, see U.S. Pat. No. 2,902,410, in particular Example 1. The $\Delta^{4,9(11)}$-17-keto steroids (I) are known, see U.S. Pat. No. 3,441,559, in particular Example 1. The 6α-fluoro-17-keto steroids (I) are known, see U.S. Pat. No. 2,838,492, in particular Examples 9 and 10. The 6α-methyl-17-keto steroids (I) are known, see U.S. Pat. No. 3,166,551, in particular Example 8. See also U.S. Pat. Nos. 2,867,630 and 3,065,146.

The 16β-methyl-17-keto steroids (I) can readily be prepared from the corresponding 17-keto steroid (I) by the processes of U.S. Pat. Nos. 3,391,169 (Examples 75, 76), 3,704,253 (column 2 and Examples 1–3) and 3,275,666.

Chart A discloses the addition of the metallated 1,2-dihaloethene

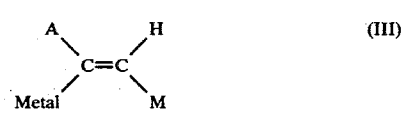

to a protected 17-keto steroid (IIa–IIe) to give the corresponding protected $C_{21}$ steroid (IVa–IVe), respectively, and subsequent hydrolysis to the 3-keto $C_{21}$ steroid (V).

The 17-keto steroid (I) must be protected at the C-3 position before reaction with the metallated 1,2-dihaloethene (III) as is well known to those skilled in the art. The androst-4-ene-3,17-diones (I) are protected as the 3-enol ether (IIa), 3-enamine (IIb) or ketal (IIc), see Chart D, where $R_3$ is alkyl of 1 thru 5 carbon atoms, with the proviso that with the ketal the $R_3$ groups can be connected to form the ethylene ketal; $R_3'$ and $R_3''$ are the same or different and are alkyl of 1 thru 5 carbon atoms. The enol ethers (IIa) are prepared by methods well known in the art, see J. Org. Chem. 26, 3925 (1961), Steroid Reactions, Edited by Carl Djerassi, Holden-Day, San Francisco 1963, page 42–45, and U.S. Pat. No. 3,516,991 (Preparation 1). The 3-enamines (IIb) are also prepared by methods well known in the art, see U.S. Pat. No. 3,629,298 and Steroid Reactions, supra, page 49–53. The ketals (IIc) are also prepared by well known methods, see Steroid Reactions, supra, page 11–14. The androsta-1,4-diene-3,17-diones (I) are protected as the 3-dialkylenamine (IId) or ketal (IIe), see Chart D.

In Chart A, the compound of formula (IIa) can be replaced by either the compound of formula (IIb or IIc), all of which by the process of the present invention will produce the corresponding intermediate compound of the formula (IVa, IVb or IVc), respectively, and the same 3-keto-$C_{21}$ steroid (V). Likewise with the $\Delta^1$ steroids, the compound of formula (IId) can be replaced by the compound of formula (IIe), which by the process of the present invention will produce the corresponding intermediate compound of the formula (IV). With compounds of formulas (IIc) and (IIe) there is a mixture of the $\Delta^4$ and $\Delta^5$ isomers. Thermodynamically the $\Delta^5$ isomer predominates and therefore is diagramed. However, the $\Delta^4$ isomer is considered equivalent of the $\Delta^5$ isomer as both react the same way with the metallated 1,2-dihaloethene (III) to produce the protected $C_{21}$ steroid (IV).

If the 17-keto starting material (I) has a $9\alpha$-hydroxy or $11\beta$-hydroxy group, these should also be protected, preferably as the silyl derivative —OSi(R)$_3$. The silyl protecting group can later be readily removed as is well known to those skilled in the art.

The metallated 1,2-dihaloethene (III) is prepared from the corresponding 1,2-dihaloethene by reaction with R-metal where R is alkyl of 1 thru 5 carbon atoms or phenyl and where metal is lithium, potassium or sodium. It is preferred that R is butyl or phenyl and metal is lithium.

The halogens include fluorine, chlorine, and bromine. It is preferred that the halogen be chlorine or bromine. It is more preferred that the halogen be chlorine. Lithiation of 1,2-dichloroethenes has been previously described, see Chem. Ber. 99, 1773 (1966) and Tetrahedron Letters 1137 (1964). The anion must be generated in a dry solvent under a nitrogen atmosphere. If oxygen or water is present, the anion will be quenched. Suitable solvents for generation of the anion include THF, 1,2-dimethoxyethane, methyl furan, tetramethylenediamine, hexamethylphosphorictriamide and dioxane, or mixtures thereof, or with other nonpolar organic solvents. It is best to use about three equivalents of the solvent used for generation of the anion per equivalent of R-metal to maintain stability of the anion. The preferred solvent is THF. The reaction is performed at $-120°$ to $-20°$, preferably $-80°$ to $-40°$, more preferably about $-60°$. Once the anion is generated, usually less than 1 hour, the reaction mixture is diluted with dry non-polar organic solvents, including hydrocarbon solvents such as pentane or hexane or aromatic solvents such as toluene or benzene or mixtures thereof. Toluene-THF and toluene-hexane-THF are the preferred solvents. However, the three equivalent amount of anion generating solvent is still necessary for stability of the generated anion. The toluene is added because the addition of the anion to the protected 17-keto steroid (II) is preferably performed in a non-polar solvent. Following dilution of the metallated 1,2-dihalogenated ethene (III) with the non-polar solvent, the protected 17-keto steroid (II) is added as a solid or in solution with mixing and the reaction is followed by TLC at about $-80°$ to $-40°$. The reaction may be warmed to about $-30°$ to facilitate completion.

If it is desired to isolate the protected $C_{21}$ steroid, the reaction is quenched, as is well known to those skilled in the art, by addition of water. The non-polar organic phase is washed with water to remove the THF and salt and is worked up as is well known to those skilled in the art. It is preferable not to isolate the protected $C_{21}$ steroid (IV) but rather convert it in situ to the 3-keto-$C_{21}$ steroid (V) by addition of a catalytic amount of an acid such as p-TSA, hydrochloric, sulfuric, phosphoric, etc., as is well known to those skilled in the art.

Chart B discloses the sulfenation of the 3-keto-$C_{21}$ steroid (V) to produce the 20,21-dihalo steroid (VII) by use of the sulfenylating agent $R_{22}$-S-X (VI) where $R_{22}$ is alkyl of 1 thru 5 carbon atoms, trichloromethyl, phenyl, or phenyl substituted with 1 thru 4 carbon atoms or substituted with 1 thru 3 nitro or trifluoromethyl groups, aralkyl of 7 thru 12 carbon atoms, or —N—($R_{122}$)$_2$ where $R_{122}$ is alkyl of 1 thru 4 carbon atoms or phenyl, or phthalimide. It is preferred that $R_{22}$ is phenyl. The group X is a chlorine or bromine atom or phenylsulfone, phthalimide or imidazole group, it is preferred that X is chlorine or bromine atom, and it is more preferred that X is chlorine.

The appropriately substituted sulfenylating agents (VI) are prepared by methods known to those skilled in the art. For example, sulfuryl chloride is added to a thiol previously dissolved in an organic solvent such as carbon tetrachloride. See Chem. Reviews, 39, 269 (1946) at page 279 and U.S. Pat. No. 2,929,820.

The sulfenation reaction is carried out in a non-polar aprotic solvent such as toluene, chloroform, ether, or methylene chloride. The reaction is carried out in the presence of at least an equal molar amount of a tertiary amine base, such as triethylamine or pyridine. With triethylamine, preferably an excess is used. Any excess base serves as additional solvent for the reaction. The reaction is preferably carried out at about $-15°$ to $0°$, but proceeds adequately in a temperature range of about $-80°$ to about $25°$. The reaction is preferably carried out under an inert dry gas such as nitrogen, argon, or carbon dioxide. The substituted sulfenyl halide (VI) is added dropwise to the reaction mixture. Following addition of the substituted sulfenylating agent to the reaction mixture, the cooling bath is removed and the temperature is allowed to rise to about $20°$; however, the temperature may be in the range of about $-30°$ to about $25°$. The excess substituted sulfenylating agent is then quenched with an appropriate quenching agent such as water, cyclohexene, various alcohols such as methanol and ethanol, or acetone. The reaction is then washed with dilute acid such as 1 N hydrochloric, sulfuric, phosphoric, acetic, etc. The concentration of the acid is not critical. The excess acid is removed with agents which are well known in the art such as sodium bicarbonate. The solvent is then removed and the product may be obtained by standard work-up.

The 20,21-dihalo steroid (VII) is transformed to the corresponding sulfoxide (VIII) by reaction with base. At least one equivalent of a base or anion such as $^\ominus OR_{20}$ or $^\ominus SR_{20}$ is used where $R_{20}$ is alkyl of 1 thru 4 carbon atoms or phenyl. The preferred bases are methoxide or phenoxide. Methoxide is most preferred. The reaction requires a polar solvent such as DMSO, DMF, THF to proceed at a good rate. The reaction goes in alcoholic solvents but proceeds more slowly.

The sulfoxide (VIII) can be isolated from the above reaction by quenching and normal work-up; however, it is preferable not to isolate the sulfoxide (VIII) but rather perform the next reaction, conversion of sulfoxide (VIII) to the corresponding 20-unsaturated steroid (IX), in situ. If one desires to isolate the sulfoxide (VIII), one equivalent base is used and the preferred solvents are DMF or THF. After addition is complete, as measured by TLC, the reaction is quenched by addition of a mild acid and is worked up as is well known to those skilled in the art.

The base catalyzed isomerization of $\beta$, $\gamma$ to $\alpha,\beta$-unsaturated sulfoxides is well known, see J. Am. Chem. Soc. 86, 3840 (1964) and the addition of nucleophiles to $\beta$-halo-$\alpha,\beta$-unsaturated sulfoxides has been previously observed in simple systems, see J. Org. Chem. 35, 2831 (1970).

If the preferred route is followed without isolation of the sulfoxide (VIII), 1.5–2.0 equivalents of base are used. In addition, the preferred solvent system is THF-acetone-methanol. Acetone acts as both a solvent and thiophile. The 20,21-dihalo steroid (VII) is cooled to about 0°, the base is added, and the sulfoxide (VIII) forms rapidly in about 5 minutes. The mixture is warmed to 20°–40°, more preferably 25°–30° and is stirred 6–20 hours and then quenched with acid.

The sulfoxide (VIII) exists as four isomers, only one of which gives exclusively the desired 20-unsaturated steroid (IX), the rest give mixtures of the undesired 17$\alpha$- and 17$\beta$-hydroxy steroids. Apparently these four isomers are in equilibrium with each other and the most reactive isomer yields the desired 20-unsaturated steroid (IX). Therefore, it is desired to use a polar solvent system in the presence of base to continuously equilibrate the undesired three isomers to produce the desired isomer as it is converted to the 20-unsaturated steroid (IX).

During the reaction involving the conversion of the sulfoxide (VIII) to the corresponding 20-unsaturated steroid (IX) it is necessary to trap the $R_{22}$-S$^\oplus$ moiety. Therefore, the reaction necessitates the use of thiophiles. The thiophile must not be nucleophilic or the Z group will be lost. Suitable thiophiles include ketones (acetone, 3-pentanone, cyclohexanone, 1-(phenylthio)acetone, 2,4-pentanedione), phosphites (trimethylphosphite), mesityl oxide, dimethyl malonate, 2,6-di-t-butylphenol, ethyl vinyl ether and dihydropyran. Ketones are preferred and acetone is the preferred ketone.

The 20-unsaturated steroid (IX) is transformed to the corresponding 21-halo steroid (X) by aqueous acid (p-TSA, hydrochloric, sulfuric or phosphoric) hydrolysis. Aqueous hydrochloric acid in methylene chloride is preferred.

The 21-halo steroid (X) is transformed to the corresponding croticoid (XI) by the process of U.S. Pat. No. 4,041,055, see column 15, lines 39–56. If the substituent at $C_{21}$ is chlorine rather than bromine, potassium iodide can be used as a catalyst. The preferred anion is acetate.

The 21-acyloxy-17$\alpha$-hydroxy-20-keto end products (XI) are useful pharmacologically active steroids and are useful intermediates in the production of other pharmacologically active corticoids. For example, 17$\alpha$,21-dihydroxypregna-4,9(11)-diene-3,20-dione 21-acetate (XI), the compound produced by Example 6, is an important intermediate in corticoid synthesis as evidenced by the fact that U.S. Pat. Nos. 3,444,559 (Examples 2, 8 and 9) and 4,041,055 (Example 66 and claims 91 and 92) disclose and claim its production.

DEFINITIONS

The definitions and explanations below are for the terms as used throughout the entire patent application including both the specification and claims.

All temperatures are in degrees Centigrade.

TLC refers to thin-layer chromatography.

THF refers to tetrahydrofuran.

DMSO refers to dimethylsulfoxide.

DMF refers to dimethylformamide.

p-TSA refers to p-toluenesulfonic acid.

NMR refers to nuclear (proton) magnetic resonance spectroscopy, chemical shifts are reported in ppm ($\delta$) downfield from TMS.

TMS refers to tetramethylsilane.

When solvent pairs are used, the ratio of solvents used are volume/volume (v/v).

A is a fluorine, chlorine or bromine atom.

M is a fluorine, chorine or bromine atom.

R is alkyl of 1 thru 5 carbon atoms or phenyl.

$R_3$ is alkyl of 1 thru 5 carbon atoms with the proviso that with the ketal (IIIc and IIIe), the $R_3$ groups can be connected to form the ethylene ketal.

Metal is lithium, sodium or potassium.

$R_3'$ is alkyl of 1 thru 5 carbon atoms.

$R_3''$ is alkyl of 1 thru 5 carbon atoms.

$R_6$ is a hydrogen or fluorine atom or methyl group.

$R_9$ is a hydrogen or fluorine atom, hydroxyl group, —OSi(R)$_3$ or nothing.

$R_{11}$ is [H], [H,H], [H, $\beta$-OH], [H, $\beta$-OSi(R)$_3$], or [O].

$R_{16}$ is a hydrogen atom or methyl group.

$R_{20}$ is alkyl of 1 thru 4 carbon atoms or phenyl.

$R_{21}$ is alkyl of 1 thru 4 carbon atoms or phenyl.

$R_{22}$ is alkyl of 1 thru 5 carbon atoms, trichloromethyl, phenyl, phenyl substituted with 1–4 carbon atoms or substituted with 1 thru 3 nitro or trifluoromethyl groups, aralkyl of 7 thru 12 carbon atoms or —N—(R$_{122}$)$_2$ or phthalimide.

$R_{122}$ is alkyl of 1 thru 4 carbon atoms, phenyl, or phthalimide.

X is a chlorine or bromine atom, phenylsulfone, phthalimide or imidazole group.

Z is —OR$_{20}$ or —SR$_{20}$.

~ indicates the attached group can be in either the $\alpha$ or $\beta$ configuration.

⋯ is a single or double bond.

When the term "alkyl of   thru   carbon atoms" is used, it includes isomers thereof when such exist.

EXAMPLES

Without further elaboration, it is believed that one skilled in the art can, using the preceding description, practice the present invention to its fullest extent. The following preferred specific embodiments are, therefore, to be construed as merely illustrative, and not limiting of the preceding disclosure in any way whatsoever.

EXAMPLE 1

17α-[1,2-(E)-dichloroethenyl]-17β-hydroxyandrostan-4,9(11)-dien-3-one (V)

Dry toluene (270 ml), dry THF (54 ml) and trans-1,2-dichloroethylene (27.9 ml) are cooled to less than −60° under nitrogen. n-Butyllithium (1.6 M, 149 ml) is added dropwise over 45 minutes to the dichloroethylene. The resulting mixture is stirred at less than −60° for 1 hour. Then 3-hydroxyandrosta-3,5,9(11)-trien-17-one 3-methyl ether (IIa, U.S. Pat. No. 3,516,991, Preparation 1, 54.0 g) is added as a solid all at once. The mixture is stirred for 1.5 hours at less than −60° and then is brought to −45° to −50° for one hour. Water (46 ml) is added and the mixture is permitted to warm to 20°–25°. The organic layer is extracted twice with water (150 ml each time) and then treated with aqueous hydrochloric acid (3 N, 5 ml). The resulting mixture is stirred vigorously for about 20 hours at 20°–25° after which it is cooled to 0°. The product is recovered by filtration and is washed with cold toluene (90 ml), then water (100 ml) and finally dried under reduced pressure to give the title compound, mp 226°–233° (decomposition); NMR (CDCl$_3$) 0.95, 1.35, 2.96, 5.55, 5.75 and 6.45δ.

EXAMPLE 2

20,21-Dichloro-21-(phenylsulfinyl)pregna-4,9(11),17(20)-trien-3-one (VII)

17α-[1,2-(E)-dichloroethenyl]-17β-hydroxyandrosta-4,9(11)-dien-3-one (V, Example 1, 4.0 g.), dry methylene chloride (45 ml) and triethylamine (5.8 ml) are mixed under nitrogen and cooled to −10° to −15°. Phenylsulfenyl chloride (1.44 M, 12 ml) in methylene chloride is added dropwise over about 45 minutes. The resulting mixture is stirred for one hour at <−10° and then is allowed to warm to 20°–25°. Water is then added and the organic layer is washed with water (15 ml). The resulting methylene chloride solution is heated to reflux with dropwise addition of heptane (40 ml) and the methylene chloride distilled off. The distillation continues until a solvent mixture of methylene chloride-heptane (10/90) is obtained. The resulting slurry is cooled to 20°–25° and the product isolated by filtration to give the title compound, m.p. 133°–133.5°; NMR (CDCl$_3$) 0.92, 1.33, 5.42, 5.57, 5.78, 7.6 and 7.87δ.

EXAMPLE 3

21-Chloro-20-methoxy-21-(phenylsulfinyl)pregna-4,9(11),17(20)-trien-3-one (VIII)

20,21-Dichloro-21-(phenylsulfinyl)pregna-4,9(11),17(20)-trien-3-one (VII, Example 2, 1.0 g), dry DMF (20 ml) and methanol (4 ml) are stirred under nitrogen and cooled to −25°. Sodium methoxide in methanol (25%, 1 ml) is added dropwise. After 30 minutes, the mixture is quenched with water (0.33 ml) and allowed to warm to 20°–25°. The product is isolated by diluting the mixture with water and extracting with ethyl acetate. The organic layer is separated and dried over sodium sulfate and then concentrated under reduced pressure to give the title compound: NMR (CDCl$_3$) 0.85, 0.87, 0.98, 1.36, 1.34, 3.89, 3.84, 5.03, 5.10, 5.23, 5.43, 5.53, 5.72, 5.75 and 7.4–8.0δ.

EXAMPLE 4

21-Chloro-17α-hydroxy-20-methoxypregna-4,9(11),20-trien-3-one (IX)

20,21-Dichloro-21-(phenylsulfinyl)pregna-4,9(11),17(20)-trien-3-one (VII, Example 2, 3.0 g) dry THF (36 ml), methanol (7.5 ml) and acetone (6 ml) are cooled to 0° under nitrogen and sodium methoxide in methanol (25%, 2.8 ml) is added with stirring. After 1 hour of stirring, TLC analysis shows complete conversion of the dichloro starting material (VI) to 21-chloro-20-methoxy-21-(phenylsulfinyl)pregna-4,9(11),17(20)-trien-3-one (VIII, Example 3). The mixture is brought to 20°–25° and stirred for 22 hours and then warmed to 30°–35° for 5 hours. The mixture is diluted with water (100 ml) and extracted with ethyl acetate-methylene chloride (2×75 ml). The organic extracts are combined, washed with water, dried over sodium sulfate and concentrated under reduced pressure. The concentrate is triturated with hexane/ethyl acetate (85/15, 25 ml) to give the title compound, mp 197°–199°; NMR (CDCl$_3$) 0.68, 1.35, 3.97, 5.55 and 5.73δ.

EXAMPLE 5

21-Chloro-17α-hydroxypregna-4,9(11)-diene-3,20-dione (X)

21-Chloro-17α-hydroxy-20-methoxypregna-4,9(11),20-trien-3-one (IX, Example 4, 1.0 g), THF (4 ml), acetone (4.9 ml), and methanol (1.4 ml) are mixed. Aqueous hydrochloric acid (6 N, 0.44 ml) is added and the resulting slurry heated at 40° for 1.5 hours. The mixture is cooled to 20°–25° and diluted with hexane (3 ml). The solids are isolated by filtration and washed with hexane/ethyl acetate (85/15, 13 ml) to give the title compound.

EXAMPLE 6

17α,21-Dihydroxypregna-4,9(11)-diene-3,20-dione 21-acetate (XI)

21-Chloro-17α-hydroxypregna-4,9(11)-diene-3,20-dione (X, Example 5, 1.0 g), anhydrous potassium acetate (340 mg), potassium iodide (114 mg), anhydrous acetone (7.5 ml) and methylene chloride (2.5 ml) are slurried and heated to 70° (closed to the atmosphere—therefore under slight pressure) for 5 to 7 hours. The reaction mixture is cooled to 20°–25° and the methylene chloride removed by reduced pressure. Acetone (3.5 ml) is added, followed by water (1.5 ml). The mixture is heated to about 70° for 30 minutes, then cooled to 0° for about 2 hours. The product is isolated by filtration and then washed with water (5 ml) and aqueous acetone (80%, 5 ml). After drying, the title compound is obtained, NMR (CDCl$_3$) 0.64, 1.33, 2.18, 4.97, 5.56 and 5.75δ.

EXAMPLE 7

21-Chloro-17α-hydroxypregna-4,9(11)-diene-3,20-dione (X)

20,21-Dichloro-21-(phenylsulfinyl)pregna-4,9(11),17(20)-trien-3-one (VII, Example 2, 3.0 g), THF (60 ml), methanol (12 ml) and acetone (9 ml) are cooled to 0° under nitrogen and sodium methoxide in methanol (25%, 2.8 ml) are added. After one hour, by TLC analysis, complete conversion to the 20-methoxy derivative (VIII) had occurred. The resulting mixture is brought to 28° and stirred for 22 hours and then warmed to 30°-35° for five hours. The mixture is diluted with water (150 ml) and then extracted with ethyl acetate-methylene chloride (2×75 ml). The organic extracts are combined, washed with water, dried over sodium sulfate and concentrated under reduced pressure. The concentrate is slurried in methylene chloride (15 ml) and treated with aqueous hydrochloric acid (6 N, 1 ml) at 30°-35° for one hour. The mixture is diluted with methylene chloride (25 ml) and extracted with water (2×10 ml). The organic layer is separated, dried over sodium sulfate and concentrated under reduced pressure to give the crude product. This material is purified by trituration with hexane/ethyl acetate (7/3, 25 ml) to give the title compound, mp 210.5°-212°; NMR (CDCl$_3$) 0.63, 1.33, 4.47, 5.53 and 5.72δ.

CHART A

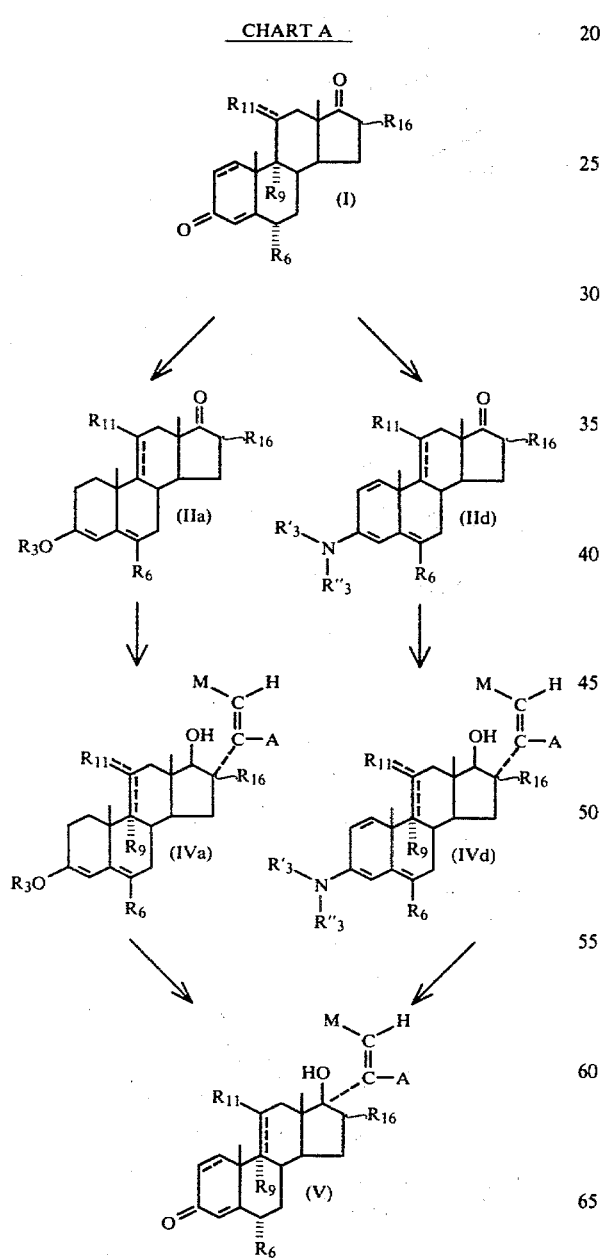

CHART B

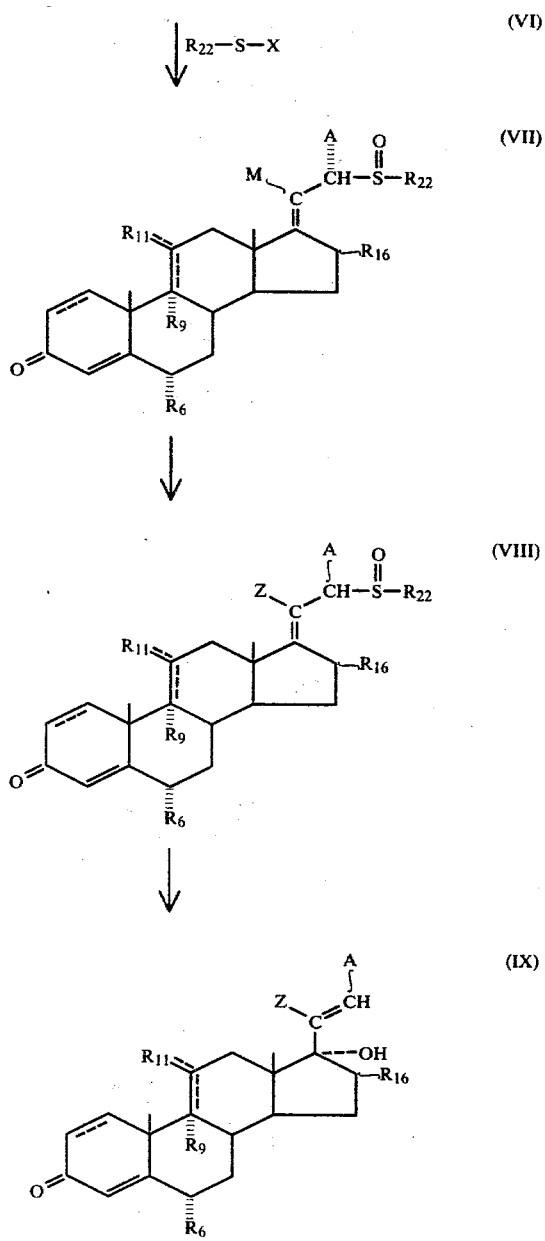

CHART C

11
-continued
CHART C
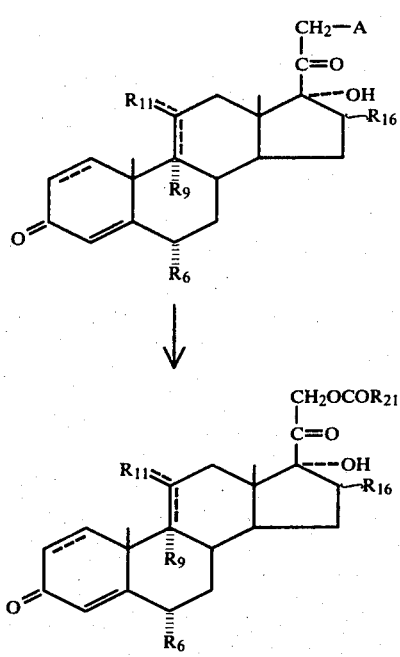
(X)
(XI)
CHART D
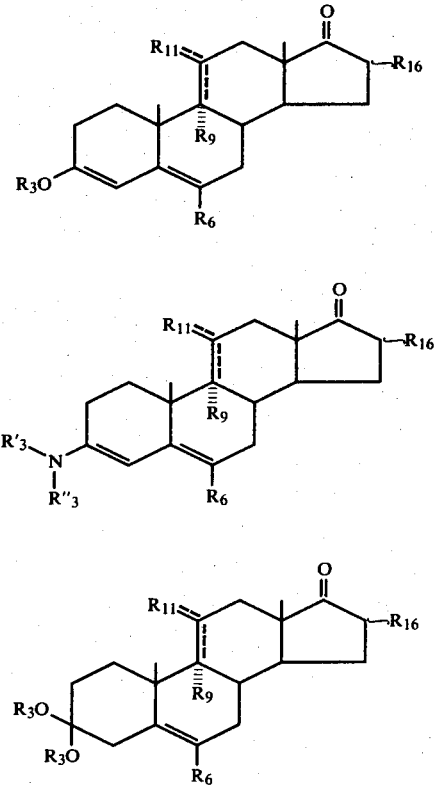
(IIa)
(IIb)
(IIc)
12
-continued
CHART D
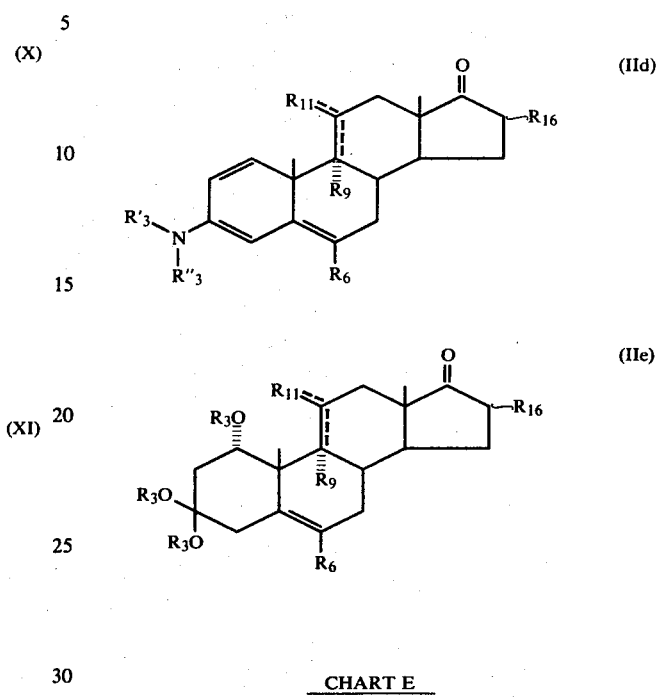
(IId)
(IIe)
CHART E
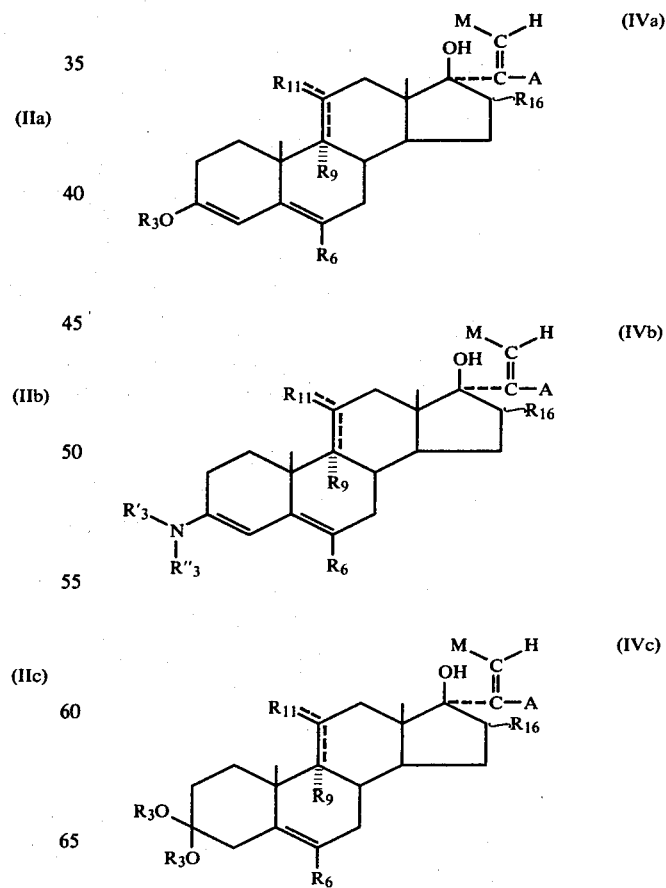
(IVa)
(IVb)
(IVc)

-continued
CHART E

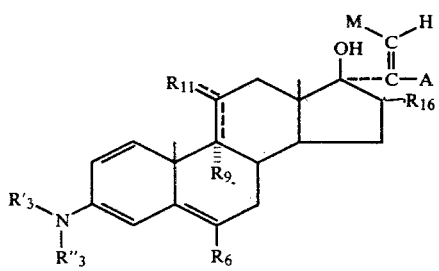
(IVd)

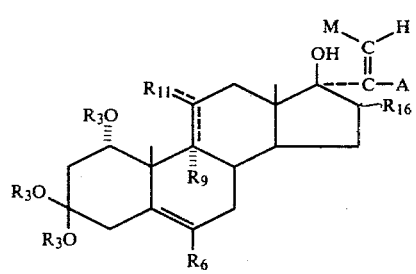
(IVa)

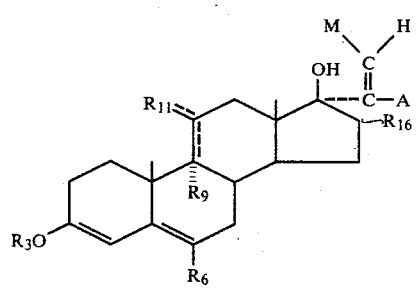
(IVb)

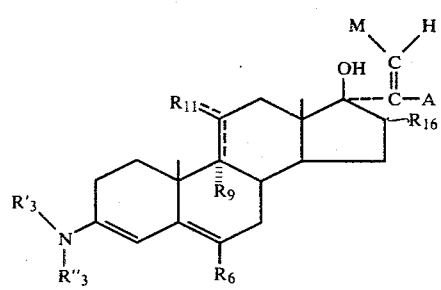
(IVc)

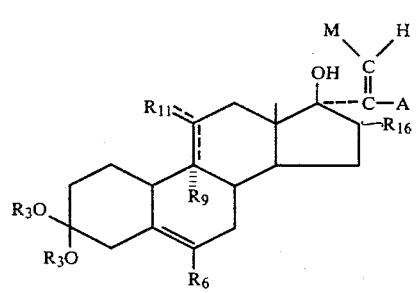

We claim:

1. A protected $C_{21}$ steroid selected from the group consisting of

-continued

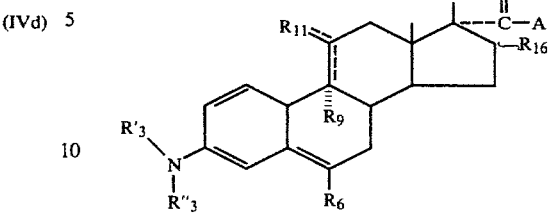
(IVd)

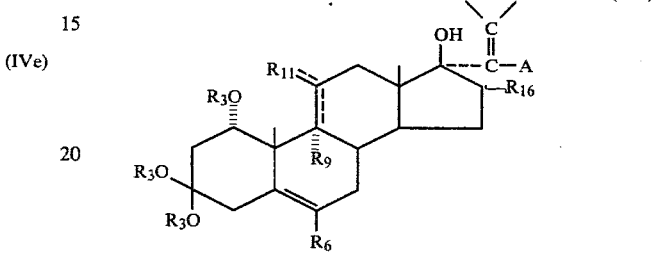
(IVe)

where A, M, $R_3$, $R_3'$, $R_3''$, $R_6$, $R_9$, $R_{11}$, $R_{16}$, ~ and ---- are defined in the specification.

2. A protected $C_{21}$ steroid according to claim 1, which is the compound of (IVa) or (IVd).

3. A protected $C_{21}$ steroid according to claim 1 where A is a chlorine atom.

4. A protected $C_{21}$ steroid according to claim 3 wherein A and M are both a chlorine atom.

5. A protected $C_{21}$ steroid of formula (IVa thru IVe) according to claim 1, wherein $R_6$ and $R_{16}$ are hydrogen atoms, where $R_9$ is nothing and $R_{11}$ is [H] which gives a $\Delta^{9,11}$ functionality in the C ring.

6. A protected $C_{21}$ steroid according to claim 1 where for the compounds of (IVa, IVc and IVe), $R_3$ is methyl and for the compounds of (IVb and IVd) $R_3'$ and $R_3''$ are methyl.

7. A 3-keto-$C_{21}$ steroid of the formula

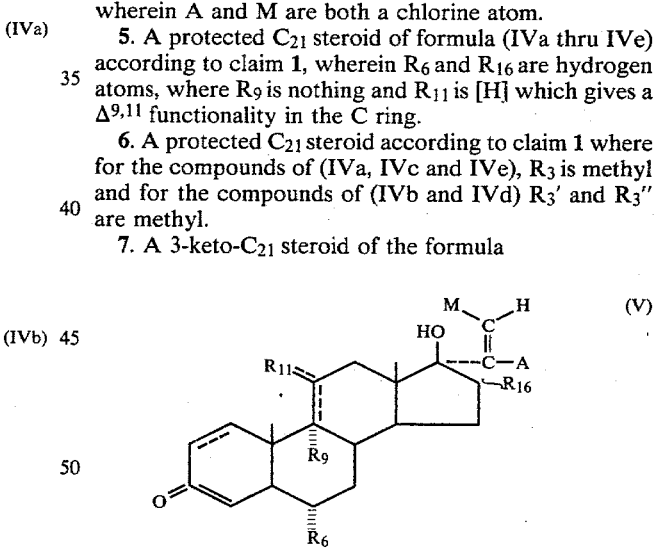
(V)

where A, M, $R_6$, $R_9$, $R_{11}$, $R_{16}$, ~ and ---- are defined in the specification.

8. A 3-keto-$C_{21}$ steroid according to claim 7 where A is a chlorine atom.

9. A 3-keto-$C_{21}$ steroid according to claim 8 where A and M are both a chlorine atom.

10. A 3-keto-$C_{21}$ steroid of formula (V) according to claim 7 where $R_6$ and $R_{16}$ are hydrogen atoms, where $R_9$ is nothing and $R_{11}$ is [H] which gives a $\Delta^{9,11}$ functionality in the C ring.

11. A 3-keto-$C_{21}$ steroid according to claim 10 which is 17α-[1,2-(E)-dichloroethenyl]-17β-hydroxyandrosta-4,9(11)-dien-3-one.

* * * * *

UNITED STATES PATENT OFFICE
CERTIFICATE OF CORRECTION

Patent No. 4,357,279         Dated November 2, 1982

Inventor(s) Jerry A. Walker et al.

It is certified that error appears in the above-identified patent and that said Letters Patent are hereby corrected as shown below:

Column 10, line 20, in formula (VII) the $C_{17}$ side chain should appear as follows:

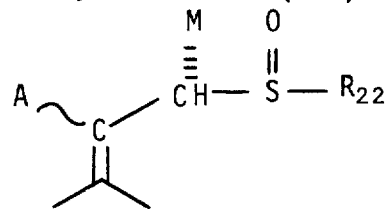

Column 10, line 35, in formula (VIII) the $C_{17}$ side chain should appear as follows:

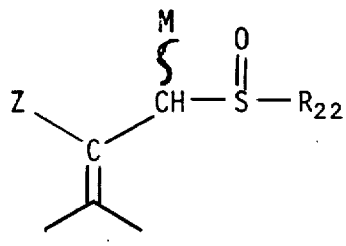

UNITED STATES PATENT OFFICE
CERTIFICATE OF CORRECTION

Patent No. 4,357,279  Dated November 2, 1982

Inventor(s) Jerry A. Walker et al.

It is certified that error appears in the above-identified patent and that said Letters Patent are hereby corrected as shown below:

Column 10, line 50, in formula (IX) the $C_{17}$ side chain should appear as follows:

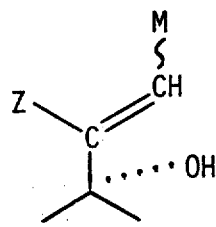

Column 11, line 10, in formula (X) the $C_{17}$ side chain should appear as follows:

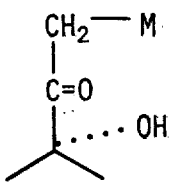

Signed and Sealed this

Ninth Day of October 1984

[SEAL]

Attest:

Attesting Officer

GERALD J. MOSSINGHOFF

Commissioner of Patents and Trademarks